United States Patent
Haskard et al.

(10) Patent No.: US 9,974,915 B2
(45) Date of Patent: May 22, 2018

(54) ELASTIC HEADGEAR

(71) Applicant: ResMed Limited, Bella Vista (AU)

(72) Inventors: Kirrily Michele Haskard, Sydney (AU); Anthony Paul Barbara, Smithfield (AU); Alicia Kristianne Wells, Narrabeen (AU)

(73) Assignee: RESMED LIMITED, Bella Vista (AU)

( * ) Notice: Subject to any disclaimer, the term of this patent is extended or adjusted under 35 U.S.C. 154(b) by 558 days.

(21) Appl. No.: 13/952,165

(22) Filed: Jul. 26, 2013

(65) Prior Publication Data

US 2014/0026890 A1      Jan. 30, 2014

Related U.S. Application Data

(60) Provisional application No. 61/676,456, filed on Jul. 27, 2012.

(51) Int. Cl.
*A61M 16/06* (2006.01)

(52) U.S. Cl.
CPC .... *A61M 16/0683* (2013.01); *A61M 16/0666* (2013.01)

(58) Field of Classification Search
CPC .......... A61M 16/0666; A61M 16/0683; A61M 16/0627; A61M 16/0694
See application file for complete search history.

(56) References Cited

U.S. PATENT DOCUMENTS

| | | | |
|---|---|---|---|
| 4,686,354 A | 8/1987 | Makin | |
| 5,181,507 A | 1/1993 | Michel et al. | |
| 5,357,948 A | 10/1994 | Eilentropp | |
| 5,438,979 A * | 8/1995 | Johnson, Jr. | A61M 16/0666 128/207.18 |
| 5,724,965 A | 3/1998 | Handke et al. | |
| 6,119,694 A | 9/2000 | Correa et al. | |
| 6,152,186 A | 11/2000 | Arney et al. | |
| 6,418,929 B1 | 7/2002 | Norfleet | |
| 7,296,575 B1 | 11/2007 | Radney | |
| 7,562,658 B2 | 7/2009 | Madaus et al. | |
| 7,743,767 B2 | 6/2010 | Ging et al. | |
| 2003/0075180 A1 | 4/2003 | Raje et al. | |
| 2004/0149280 A1 | 8/2004 | Semeniuk | |
| 2005/0109343 A1 | 5/2005 | Flannigan et al. | |
| 2006/0060200 A1 | 3/2006 | Ho et al. | |

(Continued)

FOREIGN PATENT DOCUMENTS

| | | |
|---|---|---|
| EP | 1 356 841 A2 | 10/2003 |
| EP | 1356841 | 10/2003 |

(Continued)

OTHER PUBLICATIONS

Written Opinion of the ISA for PCT/AU2013/000830 dated Sep. 9, 2014, 16 pages.

(Continued)

*Primary Examiner* — Lynne Anderson
(74) *Attorney, Agent, or Firm* — Nixon & Vanderhye, P.C.

(57) ABSTRACT

Headgear, comprising at least one strap; and at least one rigidizer, the headgear being arranged to position one of the at least one strap and one of the at least one rigidizer, with regard to one another such that the rigidizer imparts a desired shape to at least a portion of the strap while allowing said portion of the strap to move relative to the rigidizer.

44 Claims, 2 Drawing Sheets

(56) References Cited

U.S. PATENT DOCUMENTS

| | | |
|---|---|---|
| 2006/0081256 A1 | 4/2006 | Palmer |
| 2006/0096598 A1 | 5/2006 | Ho et al. |
| 2006/0169004 A1* | 8/2006 | Belluye .................. A41D 1/084 |
| | | 66/177 |
| 2009/0044808 A1 | 2/2009 | Guney et al. |
| 2009/0078259 A1 | 3/2009 | Kooij et al. |
| 2009/0107508 A1 | 4/2009 | Brambilla et al. |
| 2009/0250065 A1 | 10/2009 | Omura et al. |
| 2010/0000543 A1 | 1/2010 | Berthon-Jones et al. |
| 2010/0224276 A1 | 9/2010 | Forrester et al. |
| 2012/0204878 A1* | 8/2012 | Smith ............... A61M 16/0683 |
| | | 128/206.21 |
| 2012/0318270 A1 | 12/2012 | McAuley et al. |
| 2013/0074845 A1 | 3/2013 | Smith et al. |

FOREIGN PATENT DOCUMENTS

| | | | |
|---|---|---|---|
| EP | 2 022 528 A2 | 2/2009 | |
| EP | 2022528 | 2/2009 | |
| EP | 2027880 | 2/2009 | |
| EP | 2140902 * | 1/2010 | ............ A61M 16/06 |
| NZ | 553756 | 6/2007 | |
| NZ | 553756 A | 6/2007 | |
| NZ | 553822 A | 6/2007 | |
| NZ | 553824 | 6/2007 | |
| NZ | 553824 A | 6/2007 | |
| NZ | 553825 | 6/2007 | |
| NZ | 553825 A | 6/2007 | |
| NZ | 562418 | 11/2007 | |
| NZ | 562418 A | 11/2007 | |
| NZ | 562419 | 11/2007 | |
| NZ | 562419 A | 11/2007 | |
| RU | 2 214 295 C1 | 9/2002 | |
| RU | 2 379 075 C2 | 1/2008 | |
| WO | WO 00/69521 | 11/2000 | |
| WO | 2001/097892 | 12/2001 | |
| WO | 2002/011804 | 2/2002 | |
| WO | 2002/047749 | 6/2002 | |
| WO | WO 03/090827 | 11/2003 | |
| WO | 2004/022147 | 3/2004 | |
| WO | WO 2004/073778 | 9/2004 | |
| WO | 2006/069415 | 7/2006 | |
| WO | 2007/012140 | 2/2007 | |
| WO | 2007/022562 | 3/2007 | |
| WO | 2007/041751 | 4/2007 | |
| WO | 2007/041786 | 4/2007 | |
| WO | 2008/007985 | 1/2008 | |
| WO | 2008/011682 | 1/2008 | |
| WO | WO 2008/011683 | 1/2008 | |
| WO | WO 2009/022250 A2 | 2/2009 | |
| WO | WO 2009/052560 | 4/2009 | |
| WO | 2010/073142 | 7/2010 | |
| WO | 2011/048510 | 4/2011 | |
| WO | 2011/048519 | 4/2011 | |
| WO | 2011/110961 | 9/2011 | |
| WO | WO 2011/121466 | 10/2011 | |
| WO | 2011/142678 | 11/2011 | |
| WO | WO 2013/026091 | 2/2013 | |
| WO | 2013/042003 | 3/2013 | |

OTHER PUBLICATIONS

International Preliminary Report on Patentability for PCT/AU2013/000830 dated Nov. 25, 2014, 259 pages.
Notification of Transmittal of the International Search Report and The Written Opinion of the International Searching Authority, or the Declaration for Application No. PCT/AU2013/000830, dated Jul. 26, 2013, 27 pages.
Office Action issued in related Russian Application No. 2015105510 dated Mar. 22, 2016, (2 pages).
Written Opinion of the International Searching Authority for International Application No. PCT/AU2013/000830 dated Nov. 22, 2013, 25 pages.
Examination Report issued in European Application No. 13 822 087.6 dated Feb. 23, 2017, 7 pages.
Office Action issued in related Russian Application No. 2015105510 with English translation, dated Mar. 24, 2017, (9 pages).
Office Action issued in related Russian Application No. 2015105510 with English translation, dated Jun. 1, 2017, (7 pages).

* cited by examiner

FIG. 1
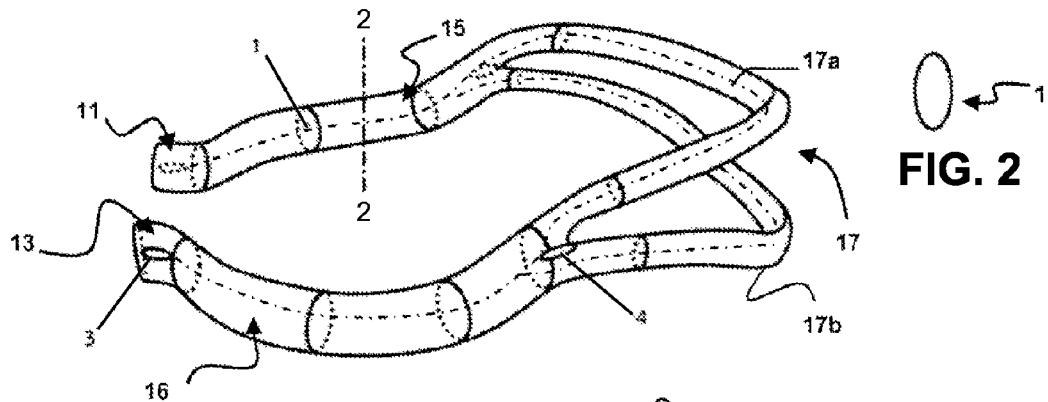
FIG. 2
FIG. 3
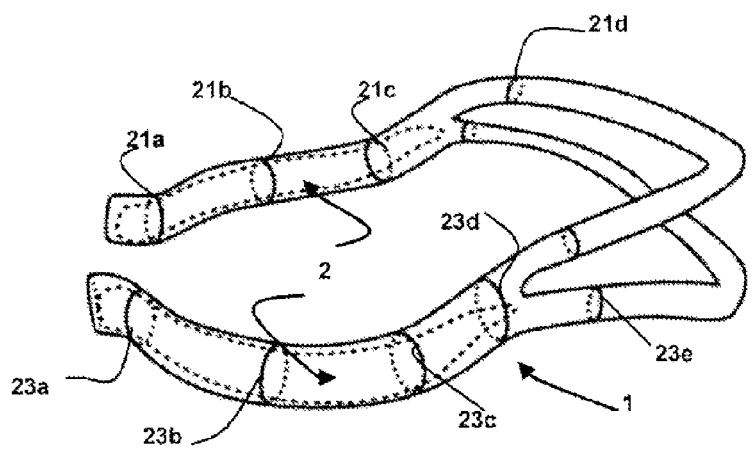
FIG. 4
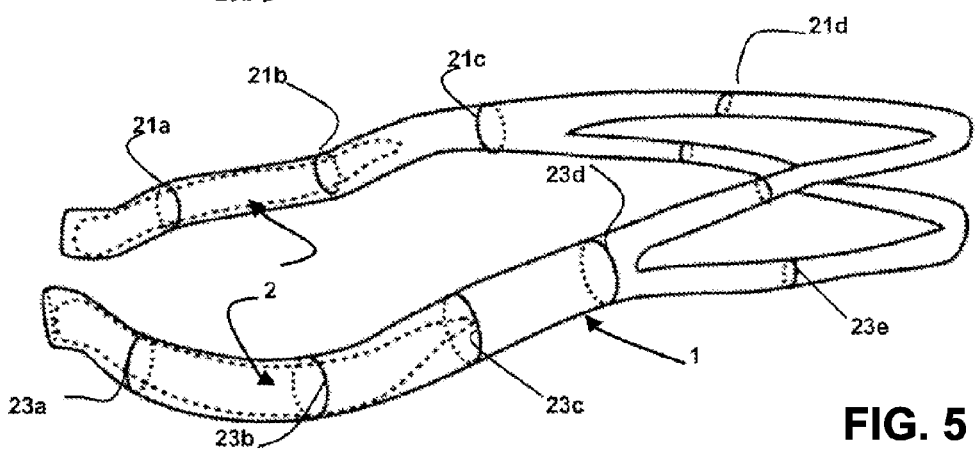
FIG. 5

ELASTIC HEADGEAR

The present application claims the benefit of U.S. Provisional Application No. 61/676,456, filed Jul. 27, 2012, which is incorporated herein by reference in its entirety.

The present invention relates to an elastic headgear, particularly for patient interfaces, particularly used in treatment of, e.g., of sleep disordered breathing (SDB) such as obstructive sleep apnea (OSA) or other breathing deficiencies.

Rigid elements, also known as "rigidizers", have been used with stretchable headgears previously. One known problem is associated with the fact that a rigidizer attached to stretchable material limits the stretchable length of the material, thus affecting the elastic properties of the entire headgear.

WO 2011/121466 discusses a flexible mask attachment element for attaching a strap to a mask. The mask attachment element includes rigid or semi-rigid mask and strap attachment portions and a flexible linkage portion there between. The flexible linkage portion is mechanically bonded or overmolded to the ends of the mask and strap apportions. The attachment element may include a pliable insert which is mechanically coupled to the attachment element at opposing sides thereof.

U.S. Pat. No. 7,562,658 refers to a headband for a respiratory mask, the headband comprising a reinforcement layer which is fixed to a padding and a cover layer by means of a stitching seam.

EP 2022528 discusses a patient interface headgear with a headgear yoke for attaching the headgear to a patient interface frame.

EP 1356841 refers to a headgear assembly for a respiratory mask comprising a yoke being attached to a strap of the headgear by adhesives or stitching.

SUMMARY

The following embodiments and aspects thereof are described and illustrated in conjunction with systems, tools and methods which are meant to be exemplary and illustrative, not limiting in scope.

The present technology is expressed by the features of the independent claims and aspects. The dependent claims and aspects refer to preferred embodiments.

The present technology relates to a headgear, particularly to a headgear for a patient interface. Such patient interface may be used in treatment of, e.g., of sleep disordered breathing (SDB) such as obstructive sleep apnea (OSA) or other deficiencies. Such treatment may include CPAP (Continuous Positive Airway Pressure), APAP (Automatic Positive Airway Pressure) or BiPAP (Bilevel Positive Airway Pressure) therapy.

The headgear comprises a strap and a rigidizer. According to a preferred aspect, the headgear is arranged to position the strap and the rigidizer with regard to one another such that the rigidizer imparts a shape, preferably a predefined shape, and/or an increased degree of rigidity, to the strap while allowing the strap to move relative to the rigidizer. Such movement may include expanding and/or contracting relative to the rigidizer. Preferably, rigidizer and strap are not affixed to one another but may, within certain bounds, float with regard to one another. In addition or alternatively, the rigidizer may be affixed to the strap in a limited area. Here, such fixation is preferably understood to define an area in which strap and rigidizer are not moveable with regard to one another. As indicated, such area is spatially limited and preferably is a point or rivet like area, a line or single stitch area, or a small area such as an areal stitch or glued area. The above named fixation techniques are cited as explaining the spatial extension of the fixation but are not understood to limit the fixation technique. Other technologies, e.g. such as may be further discussed below, are applicable. According to this aspect, the strap and the rigidizer are not affixed to one another apart from at the fixation area, the fixation being far smaller than the area of the or along which the strap and the rigidizer coextend.

The present technology advantageously allows the headgear to frame the face. In particular, the rigid element may define the headgear shape so as to direct the headgear and the associated of pressure to desired sections of the face. Moreover, the present technology advantageously allows the use of, e.g., soft comfortable textile, e.g., for the straps. Such material may be provided to touch the patient's face. The texture and fine yarn of the elastic headgear may make it moisture absorbent and comfortable on the face. Moreover, the present technology allows provision of a large fit range with one size headgear. Having the elastic able to stretch around almost the full head length may give it a lower percentage of elongation relative to the starting length. This may make it more likely to have a similar tension force in the case of a large head size to that in the case of a small head size.

Additional and/or alternative preferred aspects relate to:

1. Headgear, comprising at least one strap and at least one rigidizer, the headgear being arranged to position one of the at least one strap and one of the at least one rigidizer with regard to one another such that the rigidizer imparts a shape, preferably a predefined shape, to the strap while allowing the strap to move relative to the rigidizer.

2. Headgear according to aspect 1 wherein the rigidizer is affixed to the strap in a limited area of the rigidizer and/or in a limited area of the strap.

3. Headgear, comprising at least one strap and at least one rigidizer the rigidizer being affixed to the strap at a limited area, preferably at a point-like area, and preferably not being affixed to the strap along a length extending along a major portion of the length of the rigidizer, and preferably not being affixed to the strap along substantially the whole length.

4. Headgear according to aspects 1 or 2 combined with aspect 3.

5. Headgear according to any one of the preceding aspects, wherein the rigidizer and the strap have a substantially elongated form and wherein the rigidizer extends along at least a portion of the strap.

6. Headgear according to any one of the preceding aspects, the rigidizer being crescent shaped 7. Headgear according to any one of the preceding aspects, the rigidizer being shaped to direct the strap away from the wearer's eyes and ears.

8. Headgear according to any one of the preceding aspects, wherein the strap is made of a stretchable material and the headgear is arranged such that the strap is substantially free to move by elastically expanding and/or contracting, relative to the rigidizer, and preferably along the longitudinal axis of the strap and/or rigidizer.

9. Headgear according to any one of the preceding aspects, wherein, despite the positioning and/or affixation of the strap and the rigidizer with regard to one another, the stretchable length of the strap remains substantially unaltered vis-à-vis the strap without rigidizer.

10. Headgear according to any one of the preceding aspects, wherein the elastic headgear, is able to stretch along its substantially entire length.

11. Headgear according to any one of the preceding aspects, wherein strap and rigidizer are separate elements, preferably not or releasably attached to one another.

12a. Headgear according to any one of the preceding aspects, wherein the strap comprises retaining means, preferably a loop, sleeve and/or pocket, for receiving the rigidizer and holding the rigidizer in place.

12b. Headgear according to any one of the preceding aspects, wherein the arrangement is such that the rigidizer imparts a shape to the strap along, or in direction of, one first axis, preferably two axes (e.g. the first and a second axis), the axes being preferably substantially perpendicular to one another.

12c. Headgear according to aspect 12b, wherein the first axis substantially corresponds to the longitudinal axis of the strap and/or rigidizer, and/or wherein the first axis substantially extends along and parallel to a patients cheek or side of the head in use, and is preferably substantially horizontal; and/or
  wherein the second axis preferably extends perpendicular to the first axis and/preferably extends substantially along and parallel to a patients cheek or side of the head in use, and is preferably substantially horizontal.

12d. Headgear according to any one of the preceding aspects, wherein the arrangement is such that the rigidizer and the strap are allowed to substantially move along one axis relative to one another and/or wherein the strap is able to expand and/or contract along along one axis relative to the rigidizer.

12e. Headgear according to aspect 12d, wherein said axis preferably substantially corresponds to the first axis of the strap and/or rigidizer.

12f. Headgear according to any one of the preceding aspects, wherein the arrangement is such that the rigidizer and the strap are not allowed to substantially move relative to one another along at least one, preferably two axes, the axes preferably extending substantially perpendicular to one another.

12g. Headgear according to aspect 12f, wherein said axes are preferably substantially perpendicular to the first axis, the first axis substantially corresponding to the longitudinal axis of the strap and/or rigidizer.

13. Headgear according to any one of the preceding aspects, wherein the strap comprises a sleeve for holding the rigidizer in place and at least one opening, for receiving the rigidizer into the sleeve.

14. Headgear according to any one of the preceding aspects, wherein the headgear comprises two pockets, for receiving opposite ends of the rigidizer to retain the rigidizer in place.

15. Headgear according to any one of the preceding aspects, wherein retaining means are formed on or in the strap.

16. Headgear according to any one of the preceding aspects, wherein the strap comprises a sleeve to receive and hold the rigidizer, wherein the sleeve and the rigidizer are arranged to allow the rigidizer to move substantially axially inside the sleeve.

17. Headgear according to any one of the preceding aspects, wherein the strap comprises a sleeve to receive the rigidizer, and, preferably, wherein the headgear, particularly the sleeve and the rigidizer are adapted to allow the rigidizer to float generally unrestricted alongside the sleeve.

18. Headgear according to any one of the preceding aspects, wherein the headgear takes the shape of the rigidizer, and particularly, wherein the rigidizer and/or the strap are adapted to impart a required shape which directs the pressure of the headgear to required portions of a wearers' face.

19. Headgear according to any one of the preceding aspects, wherein the connection between the rigidizer and the headgear is localized in a limited area, such as adjacent a pocket or sleeve opening.

20. Headgear according to any one of the preceding aspects, wherein the strap comprises a sleeve arranged to receive and hold the rigidizer and/or wherein an end portion of the rigidizer is affixed to the strap.

21. Headgear according to any one of the preceding aspects, wherein the fixation is achieved by way of sowing, welding, gluing, heat staking, clamping, buttoning, snapping a cover over the end and/or snapping on an external part.

22. Headgear according to aspect 21, wherein snapping on an external part may be achieved by aligning the strap and the rigidizer, preferably by pushing the rigid element inside the sleeve and fixing both sleeve and rigid element to an external component.

23. Headgear according to aspect 22, wherein the external component preferably is an external clip that holds both the headgear sleeve and the respective end of the rigid element, and wherein, further preferably, the clip is adapted to attach the end of the headgear to a respective end of a mask frame, wherein, preferably, the clip may be a part of the mask frame itself.

24. Headgear according to any one of the preceding aspects, wherein the point at which the rigidizer is affixed to the strap is located at one end of the rigidizer.

25. Headgear according to any one of the preceding aspects, wherein multiple points for attachment may be provided such that the one or more fixation locations may be chosen and varied, preferably allowing adjustment of the strap's elastic length 26. Headgear according to any one of the preceding aspects, the strap being made of a stretchable, preferably elastic, material.

27. Headgear according to any one of the preceding aspects, wherein the rigidizer is relatively rigid, particularly as compared to the rigidity of the strap.

28. Headgear according to any one of the preceding aspects, wherein the strap is made of an elastomeric material, such as elastane, TPE, silicone etc. or a combination of any of these materials with one another or with other materials.

29. Headgear according to any one of the preceding aspects, wherein the elastic walls of the headgear are woven, knitted, braided, molded, and/or extruded.

30. Headgear according to any one of the preceding aspects, wherein the headgear comprises two or more rigidizers, preferably symmetrically disposed on both side of the patient's face.

31. Headgear according to any one of the preceding aspects, wherein the rigidizer is adapted and/or arranged to direct the headgear straps around and away from the wearer's eyes and ears 32. Headgear according to any one of the preceding aspects, wherein the headgear effectively frames the face.

33. Headgear according to any one of the preceding aspects, wherein the headgear, preferably the strap, is flexible, easy to fit, and/or has a soft touch, preferably provided by textile nature 34. Headgear according to any one of the preceding aspects, wherein the headgear, preferably the strap, is made of stretchable textile.

35. Headgear according to any one of the preceding aspects, wherein the rigidizer is removable.

36. Headgear according to any one of the preceding aspects, wherein the headgear maintains its entire operational length and is able to freely stretch along the rigid element.

37. Headgear according to any one of the preceding aspects, wherein the strap is stretchable and is in the form of a sleeve arranged to slip over the rigidiser, the arrangement being such that the strap maintains its substantially entire stretchable length and is able to substantially freely stretch over the rigidizer.

38. Headgear according to any one of the preceding aspects, wherein the headgear comprises more than two straps, a respective end of each strap being arranged for hinged connection to another strap and/or a patient interface.

39. Headgear according to any one of the preceding aspects, wherein the headgear comprises more than two straps, each strap comprising an at least partially enclosed rigidizer and wherein a respective end of each rigidizer is arranged for hinged connection to a patient interface.

40. Headgear according to any one of the preceding aspects, wherein the headgear is arranged to support a patient interface, comprising one of a nasal cannula, nasal prongs or a respiratory mask covering nose and/or mouth of a wearer, to a patient's face.

41. Headgear according to any one of the preceding aspects, wherein the strap is a hollow tube with at least one, preferably two, opening to receive the rigidizer.

42. Headgear according to any one of the preceding aspects, the headgear comprising two side straps, preferably for extending from a patient interface along the sides of a user's head, and two elastic back straps, preferably extending along the back of the user's head.

43. Headgear according to any one of the preceding aspects, the headgear comprising two back straps at the back of the head, said back straps preferably being smaller than the remaining headgear straps and, preferably, may be equal in length.

44. Headgear according to aspect 40, the back straps being not adjustable except through the elasticity of the material or through increasing both in tightness equally by shortening the total length at the arms of the headgear.

45. Headgear according to any one of the preceding aspects, comprising three, four or more separate straps connected by two or more joins.

46. Headgear according to any one of the preceding aspects, wherein rigidizer is affixed to strap at one localized point or area only, while a guiding element is provided to the strap.

47. Headgear according to aspect 45, wherein the guiding element is a loop- or sheath-like portion or passage or a pocket into which or through which the rigidizer extends.

48. Headgear according to aspect 45 or 46, wherein the guiding element allows longitudinal expansion or retraction of the strap vis-à-vis the rigidizer and/or allows free movement or floating of the rigidizer vis-à-vis the strap.

49. Strap for a headgear according to any one of the preceding aspects, and particularly with the features of the headgear strap of any one of the preceding aspects.

50. Rigidizer for a headgear according to any one of the preceding aspects, and particularly with the features of the rigidizer of any one of the preceding aspects.

In addition to the exemplary aspects and embodiments described above, further aspects and embodiments will become apparent by reference to the figures and by study of the following detailed descriptions.

The above embodiments may also provide different individual or combined advantages with regard to the patient, the physician and/or from a manufacturing point of view. Particularly for the patient, the present technology may be of particular advantage in that the headgear allows easy donning and doffing. It may also, on the one hand, provide soft textile on both sides whilst, on the other hand, allow the headgear to be guided around the eyes and ears to frame the face. The headgear allows intuitive flexible adjustment, particularly through using elasticity. It allows provision of a shape and structure that removes occlusions from the area of the eyes, for vision and ears for comfort. Also, the technology may allow utilizing the advantages of using a rigidizer, without having to use a smaller length of elastic material in the headgear. This is particularly facilitated by the fact that the elastic sleeve can stretch on the outside of the rigidizer.

Also, particularly from a physician's point of view, the technology may be of particular advantage in that it provides a large fit range with one size headgear. Also, the ability to fit the mask to patient heads of various sizes without adjustment may be more easily achieved. Advantageously, the softness in the headgear tension may allow reseating of the cushion and adjustment whilst on the patients face without causing discomfort.

Particularly from a manufacturing point of view, the present technology provides a simple one piece headgear which may go along with less inventory cost for stocking multiple sizes. The assembly efforts may be reduced as may be the use of, e.g., Velcro connections so that products no longer accidently attach to each other or to other materials. In manufacturing, less noise hazards for employees from ultrasonic cutting may be required and a reduced dust and fabric particle contamination from cutting may be achieved. The technology may also allow for use of improved colour concepts and opportunities for branding. The custom made per part textile allows colour and design to be added including graphics and branding. This is may be done by way of weaving. Other processes, such as printing, may also be used.

The proposed headgear arrangement utilizes the support provided by more rigid elements without compromising the elastic properties of the headgear and the comfort of the patient. In particular, the proposed headgear uses relatively rigid supporting elements to direct the headgear straps around and away from the eyes and ears, thus ensuring comfort and/or an unobstructed eye sight. The headgear effectively frames the face and provides a good support for the mask. At the same time, the stretchable length of the headgear remains substantially unaltered, keeping the headgear flexible and easy to fit, with a soft touch provided by its textile nature.

BRIEF DESCRIPTION OF THE FIGURES

Exemplary embodiments are illustrated in referenced figures. It is intended that the embodiments and figures disclosed herein are to be considered illustrative, rather than restrictive. The disclosure, however, both as to organization and method of operation, together with objects, features, and advantages thereof, may best be understood by reference to the following detailed description when read with the accompanying figures, in which:

FIG. 1 shows a schematic perspective view of a headgear strap in accordance with an embodiment of the present technology;

FIG. 2 shows a cross-sectional view of said headgear strap taken along line 2-2 in FIG. 1;

FIG. 3 shows a schematic side view of an exemplary embodiment of a rigidizer for the headgear in accordance with the present technology;

FIG. 4 shows a headgear with a strap containing a rigidizer in accordance with the present technology in an un-stretched state;

FIG. 5 shows the headgear of FIG. 4 in a stretched or expanded state; and

Figure 6:
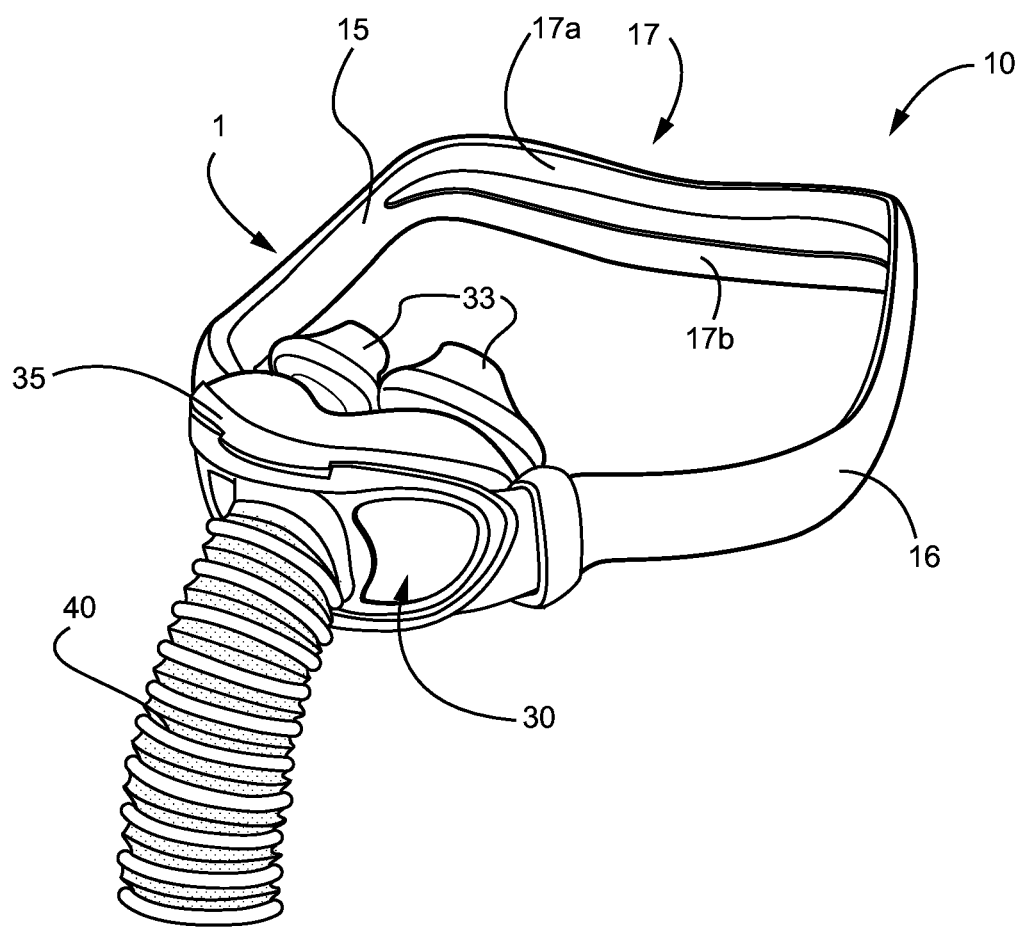
FIG. 6 shows a schematic three-dimensional view of a headgear in accordance with the present technology connected to a patient interface.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

The headgear 10 comprises a strap 1 (see, e.g., FIG. 1) and a rigid element or rigidizer 2 (see, e.g., FIG. 3). The strap is preferably made of an elastic material and has elastic properties. In other words, the strap may be elastically stretched, e.g., by a stretching force and, upon release of the stretching force, returns or contracts to its original length. The strap may be made of or comprise any elastomeric material such as elastane, TPE, silicone etc. The strap material may also represent a combination of any of the above materials with other materials. The strap may be a single layer or multilayer strap. The sides of the strap, particularly the sides for contacting the patient during use, may be woven, knitted, braided, molded, extruded or otherwise formed. This may be achieved by the strap being made of or comprising a layer of a material exhibiting the respective properties. Preferably, the strap comprises or is made of a textile material such as a woven material. Such material may comprise artificial or natural fibers for, on the one hand providing desired and beneficial surface properties such as tactile properties. On the other hand, the strap material may include elastomeric material for providing the desired elastomeric properties.

In the Figures, strap 1 is shown as being one strap 1 with two ends 11, 13 for being attached, directly or via a connector, to a patient interface. However, it may be appreciated that strap 1 may comprise multiple individual straps which are or may be connected to one another. In the Figures, the strap/headgear is shown without any adjustment or variation means. Such adjustment may be provided, however, by varying where the strap is secured to a patient interface or other rigid elements such as a connector. In addition or alternatively, adjustment could be allowed by adding a mechanism, such as slide over ladder lock clips in on the back or side straps or by otherwise adjusting the elastic length of the strap 1 and headgear 10, respectively. In the shown embodiment, strap 1 has a tube-like configuration as can be taken from the respective schematic views indicating an oval or circular shape or respective marks 21, 23 of circular or oval shape indicating the (visible) outer surface facing towards the viewer as solid and the (invisible) inner wall facing away from the viewer in dashed lines, as well as by the cross-sectional view according to FIG. 2. However, it will be appreciated that the headgear may take any other shape such as flat or sheet-like shape, single, multi-layer or laminate construction. The strap 1 may have a longitudinal axis which may be understood to be the axis substantially parallel to the paper plane, along which the strap extends (see, e.g., dashed line in FIG. 1).

FIG. 3 shows a preferred exemplary embodiment of a rigidizer or rigid element 2. As shown, the rigidizer 2 may take a crescent or semi-circular shape. Preferably, rigidizer 2 has a generally elongate and flat configuration. In other words, rigidizer 2 is far longer and wider (direction from top to bottom in the paper plane) than thick (direction into the paper plane). The ends 19a, 19b of rigidizer 2 are preferably rounded and/or slightly angled vis-à-vis the remainder of the rigidizer 2. While the rigidizer may be flat, as indicated by the paper plane in FIG. 3, it will be appreciated, that the rigidizer may have a desired spatial configuration also in the direction into the paper plane in FIG. 3, particularly in order to allow improved alignment with the shape of a user's face, such as the shape of a user's cheek or head side region (see, e.g., FIGS. 4 and 5). The rigidizer 2 may have a longitudinal axis which may be understood to be the axis substantially parallel to the paper plane, along which the rigidizer extends (see dashed line in FIG. 3).

The rigidizer 2 is more rigid, preferably substantially more rigid, than the strap 1. In particular, the rigidizer 2 and/or strap 1 are such that in combination the rigidizer imparts a shape, and preferably an increased degree of rigidity in at least one direction or in or around at least one axis, to the strap. In the shown embodiment, strap 1 has a tube- or sleeve-like configuration. Strap 1 comprises side portions 15, 16 and a back portion 17. Side portions 15, 16 are adapted to extend along the sides of a user's head when being worn while back portion 17 is adapted to extend along a user's back head. Back portion 17 may be comprised of one strap or one part of strap 1 or could include two, three or more straps running in parallel, particularly for stability. In the shown embodiment, side portions 15, 16 of strap 1 bifurcate into two back portions 17a, 17b.

Side portions 15, 16 of strap 1 each include two openings or insertion points 3, 4. The openings, preferably located at the outer surface of strap 1, i.e., the surface facing away from the patient when being worn, are adapted to receive rigidizer 2 in order to place rigidizer 2 into the interior of tube- or sleeve-like strap 1 or to remove it therefrom. Preferably, openings 3, 4 are oriented and/or shaped such that rigidizer 2 may be inserted and/or extracted through such opening in order to assemble the headgear while still preventing accidental removal or separation of rigidizer 2 from strap 1 during use. As shown in FIG. 1, this may be achieved by providing openings having a slit-like configuration, e.g., similar to button holes, which may be oriented alongside or transversely to the sleeve or strap 1. In other words, the elongate extension of the opening preferably extends substantially coaxial to the longitudinal axis of both strap 1 and rigidizer 2. This allows, particularly due to the elasticity of strap 1, an easy insertion of the rigidizer into the tube- or sleeve-like strap or part of strap 1 while, at the same time, preventing its accidental removal.

As shown, the rigid element 2 may be inserted into first insertion point 3 of the sleeve formed by the elastic headgear 1. The inserted end of the rigid element 2 is pushed further inside the sleeve until the entire rigid element is inserted into the strap 1. Once inserted in the headgear, the rigid element 2 may be left floating generally unrestricted inside the sleeve.

In addition or alternatively, the rigidizer 2 is affixed to the sleeve 1. Preferably, the affixing is effected by attaching or affixing the second end of the rigid element 2, which after the insertion is near the opening 3, to the strap 2 of the headgear. The fixation is preferably localized, as discussed in the introductory portion of the application. Here, the connection between the rigidizer and the headgear is not distributed along the length of the headgear, but is localized in the area adjacent opening 3. Alternatively, such connection may be established in the area adjacent opening 4. The affixing may be performed by way of sowing, welding, gluing, heat staking, clamping, buttoning, snapping a cover over the end or snapping on an external part by pushing the rigid element inside the sleeve and fixing both sleeve and rigid element to an external component, such as an external clip that holds both the headgear sleeve and the respective end of the rigid element. The clip may also be used to attach the end of the headgear to a respective end of a mask frame. As such, the clip may be a part of the mask frame itself.

With the present technology, while the elastic headgear sleeve is arranged to take the shape of the rigid element, it is still able to stretch along its entire length. Thus, the rigid element imparts the required shape which directs the pressure of the headgear to the required portions of the face, while the elastic headgear maintains its entire operational length and is able to freely stretch over the rigid element. At the same time, the textile sleeve of the headgear may cover the rigid element 2 and provides a soft feel and enhanced comfort.

As can be seen in FIG. 4, showing two rigidizers 2 being inserted into side portions 15, 16 of the strap 1 of the headgear 10, rigidizer 2 is held in place by the surrounding strap 1 while at the same time being able to freely float inside the sleeve-like configuration of strap 1. In some embodiments, a limitation on the movement of the rigidizer 2 is generally imposed when one of ends 19a or 19b moves towards and abuts against a respective end of the sleeve 1. For example, when the headgear is not on patient head and the straps are loose, when the inserted rigidizer 2 moves too far towards the back straps portions 17a and 17b, its end 19b may enter the open end of one of these back strap portions. As the width of the bask strap portions is smaller than that of the rigidizer, the end 19b of the rigidizer abuts against the respective backstrap, which restricts its further movement in this direction.

Rigidizer 2 may thus be allowed to move generally unrestrictedly along the length of the sleeve or be attached to the sleeve 1, preferably adjacent one of its ends.

The discussed configurations allow, as shown in FIG. 5, the strap 1 and thus headgear 10 to stretch and expand in length. Such elongation is not limited to those portions of strap 1 which are not in contact with or parallel to rigidizer 2 but also, elongation, particularly elastic elongation of strap 1, is achieved in the area of rigidizer 2. This can easily be derived from comparison of the length of rigidizer 2 in FIGS. 4 and 5 (which remains the same although strap 1 being stretched) with marks 21, 23 visualizing the length of strap 1 with regard to the length of rigidizer 2. It is easily derivable by comparison of FIGS. 4 and 5 that rigidizers 2 extend along marks 21a to 21c and 23a to 23d, respectively in FIG. 4 in the un-stretched state. Contrary thereto, in the stretched state according to FIG. 5, rigidizers 2 extend along marks 21a to 21b and 23a to 23c, only. Therefrom, it becomes clear that strap 1 is stretched also in and along the area where rigidizers 2 are contained in strap 1. Rigidizers 2 remain un-stretched.

Although being shown and discussed with regard to the specific exemplary embodiment shown in FIGS. 1 to 5, it will be appreciated that strap 1, or each of strap side portions 15, 16 may be provided with one hole or insertion point 3 or 4 only. Alternatively or in addition, strap 1 may not be tube- or sleeve-like but may have a flat single or laminate layer configuration. Here rigidizer 2 may be positioned relative to strap 1 by the provision of one or more loops, sleeve-like portions or pockets provided at the outer surface (preferably the surface facing away from the patient in use) of strap 1.

In addition or alternatively, combinations of the different connection mechanisms described herein may be provided. For example, rigidizer 2 may be fixed to the strap 1 at a single point or localized area, as discussed above, adjacent, e.g. ends 11, 13 of strap 1 while being hold next to strap 1 by provision of a loop or sleeve-like element provided at the outer surface of tube 1, preferably, e.g., in the area of mark 21b, 23b. In other words, rigidizer 2 may be connected to strap 1 by fixing it at one localized point or area only, while providing an additional guiding element to strap 1. Such guiding element may be a loop- or sheath-like portion or passage or a pocket into which or through which rigidizer 2 extends. Alternatively, the rigidizer may be disposed unattached into one or more pockets (e.g., a single open-ended pocket of sheath of appreciable length supporting the rigidizer somewhere in the middle, or a pair of pockets, each supporting a respective end of the rigidizer), or a plurality of loops distributed along the length of the strap. Such a guiding element, whether attached at one end or not, allows substantially free movement or floating of the rigidizer vis-à-vis the strap. Such configuration would allow the same advantages and benefits as the configuration discussed above.

In the shown and discussed embodiments, rigidizer 2 does not extend beyond the end(s) of strap 1. However, according to alternative preferred aspects, rigidizer 2 may be, e.g., fixed to strap 1, preferably at a point or area adjacent end 11, 13 while extending beyond strap 1. In such configuration, rigidizer 2 may impart shape or geometry and/or rigidity to strap 1 and at the same time, provide structural means such, as a connector, for connecting with a patient interface. This allows rigidizer 2 to function both as rigidizer as well as connector for connecting strap 1 and headgear 10, respectively, to a patient interface.

As will be appreciated, headgear 10 may comprise one, two or more rigidizers. While the above discussion concentrates on the relationship of a rigidizer 2 with a strap 1, it is to be noted that the shown preferred embodiment comprises two rigidizers 1, one being provided in one side portion 15, 16 of strap 1. The above comments, although eventually referring to a or one rigidizer 2, thus equally apply to two or more rigidizers 2.

FIG. 6 shows an exemplary preferred embodiment of the present technology. Here, headgear 10 comprises a strap 1 with side strap portions 15, 16 and a back strap portion 17 comprising two straps 17a, 17b running in parallel along the back of a patient's head. Headgear 10 comprises two rigidizers (not shown), each contained in a respective side portion 15 of 16 of the sleeve- or tube-like strap 1. Rigidizers 2 impart a desired shape and/or rigidity to strap 1 and thus headgear 10. In the shown embodiment, for example, side portions 15, 16 of strap 1 have a certain curvature for following a desired contour around a patient's face (see curvature at reference numerals 1 and 16), which is achieved by the provision of respectively shaped rigidizers 2. In the shown embodiment, headgear 10 is connected to patient interface 30 comprising nasal prongs 33 for providing breathable gas such as air, eventually pressurized breathable gas, to a patient's airways. In the shown embodiment, such breathable gas is provided via tube or hose 40 connected to patient interface 30. Tube 40 may be, at its other end (not shown) connected to a source of breathable gas, such as a blower or ventilator for providing pressurized breathable gas. Patient interface 30 may comprise a frame or frame portion 35 for imparting structural integrity to the patient interface and/or for connecting to headgear 10. Headgear 10 may be connected to the patient interface 30 via a separate connector means (not shown) provided on strap 1 and/or rigidizer 2.

According to a preferred aspect, the structure of strap 1 and headgear 10 is of advantage. In particular, the provision of two elastic straps or strap portions 17a, 17b at the back allows the head to be cupped and the tension vector/s to be adjusted by suitably positioning them, e.g. by spreading. The provision of two back straps 17a and 17b also allows better support and stability, as well as increased flexibility in avoiding specifically sensitive regions of the back of the head.

The two smaller straps or strap portions 17a, 17b at the back of the head may be equal in length and not adjustable except through the elasticity of the material or through increasing both in tightness equally by shortening the total length at the arms of the headgear. For example, a sliding mechanism (not shown) may be provided that allows the straps to be overlapped to a different extent, thus changing the overall length of the headgear. Symmetrical and non-independently adjustable strap lengths allow the two straps to naturally center themselves on the crown of the head. This reduces the possibility of manually over tightening one strap to compensate for the other being too loose, resulting in a misfit of the headgear.

As indicated above, two or more joins could be provided creating the headgear from three, four or more separate straps rather than strap 1 being one continuous piece. This might complicate the assembly, but may simplify the manufacturing process. Joins may preferably be placed at the bifurcation or V-junction between the side arms 15, 16 and two back straps 17a, 17b or centered at the back. The Join may be sewn, welded, glued, or over molded and could incorporate a high friction material to help reduce movement on the head.

High friction materials may also be added to the inside surface of the back and side straps 15, 16, 17a, 17b, preferably to reduce straps slipping. For the arms or side straps 15, 16 this would help the headgear stay on the cheeks and at the back strap 17 it could stop the headgear sliding across the back of the head. Such material may be printed, cast or molded onto the surface or incorporated into joins, sewing or welding processes as mentioned above.

Instead of being inserted from the opening 3 located close to the mask, as shown in the Figures, the rigidizer 2 could be inserted from the second opening 4 at the split end where the headgear strap bifurcates. Once the rigidizer 2 is inserted, the elasticity of the material could be used to hook back the rigidizer 2 inside the opening of one of the small back straps 17a, 17b (upper or lower). This may prevent the rigidizer 2 from moving, thus securing it in place. Otherwise the opening at figure could be sewn, molded or otherwise closed permanently in order to trap the rigid element inside the tube.

The split section at the back may include two, three or more straps for stability. A headgear similar to the described, may be used with full face or nasal masks also.

With the use of the present technology, the provision and use of rigidizers does/do not affect the stretchable length of the headgear straps. This preferably allows the headgear to fit a large range of head sizes. This may effectively be a "One size fits all" headgear, which means that the out of the bag headgear is more likely to fit a patient even if the patient has not tried the headgear. The present technology may provide a headgear that allows easy donning and doffing of the headgear. In particular, this may mean that, unlike some other headgears, the tension settings do not have to change and/or are not lost when the mask is removed. The rigid elements may define a desired shape that ensures that there is clearance around the eyes and ears for comfort and visibility. The textile may allow the skin to breathe and sweat naturally without silicone, foam or plastics creating and retaining surface heat.

The provision of two elastic straps at the back may allow the head to be cupped and the distribution of the applied force to be adjusted by spreading them and independently changing their position. The two smaller straps at the back of the head may be equal in length and not adjustable except through the elasticity of the material or through increasing both in tightness equally by shortening the total length at the arms of the headgear. Symmetrical and non-independently adjustable strap lengths may allow the two straps to naturally center themselves on the crown of the head. This may reduce the possibility of manually over tightening one strap to compensate for the other being too loose resulting in a misfit of the headgear. This, again, might not only lead do discomfort but also negatively influence therapy compliance.

It will be appreciated by the skilled person that the rigidizer as referred to herein is preferably more rigid than the strap and allows to impart a shape to the strap. Preferably, the rigidizer is more rigid in or around at least one axis. Alternatively, the rigidizer may be a yoke and/or a stiffener. A yoke may be understood to be a rigid element adapted to support the headgear straps. A rigidizer may be understood to be a rigid element shaping the headgear straps when worn on the face.

While the disclosure has been illustrated and described in detail in the drawings and foregoing description, such illustration and description are to be considered illustrative or exemplary and non-restrictive; the disclosure is thus not limited to the disclosed embodiments. Variations to the disclosed embodiments can be understood and effected by those skilled in the art and practicing the claimed disclosure, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

What is claimed is:

1. A patient interface system for providing pressurized breathable gas to a patient's airways to provide Continuous Positive Airway Pressure (CPAP) therapy to a patient for treatment of sleep disordered breathing (SDB), the patient interface system comprising:

a patient interface including a cushion and a mask frame;

headgear configured to retain the patient interface on the patient's face during therapy, the headgear comprising at least one strap made of an elastic material; and at least one rigidizer having a first free end opposite to and distal from the mask frame, and the at least one rigidizer having a second free end opposite to the first free end and proximate to the mask frame, wherein the at least one strap further comprises a free end that encloses and abuts the second free end of the at least one rigidizer to limit movement of the at least one strap relative to the at least one rigidizer at the second free end in use, and wherein a length of the at least one strap is adjustable to fit a range of head sizes by stretching a first portion of the at least one strap past the first free end of the at least one rigidizer.

2. A patient interface system according to claim 1, wherein the at least one rigidizer is fixed to the at least one strap in a limited area.

3. A patient interface system according to claim 1, wherein the at least one rigidizer and the at least one strap have a substantially elongated form, and wherein the at least one rigidizer extends along at least the first portion of the at least one strap.

4. A patient interface system according to claim 1, wherein the at least one rigidizer is crescent shaped.

5. A patient interface system according to claim 1, wherein the at least one rigidizer is shaped to direct the strap away from the patient's eyes and ears and between the patient's eyes and ears.

6. A patient interface system according to claim 1, wherein the headgear is arranged such that the at least one strap is substantially free to move by elastically expanding and/or elastically contracting relative to the at least one rigidizer and along a longitudinal axis of the at least one strap and/or the at least one rigidizer.

7. A patient interface system according to claim 1, wherein a stretchable length of the at least one strap remains substantially unaltered regardless of positioning and/or fixation of the at least one strap and the at least one rigidizer relative to one another.

8. A patient interface system according to claim 1, wherein, the at least one strap is elastically expandable from an original shape due to a stretching force applied to the strap, said elastic material being configured to contract to the original shape upon release of the stretching force.

9. A patient interface system according to claim 1, wherein the at least one strap comprises retaining means, including a loop, a sleeve, and/or a pocket structured to receive and hold the at least one rigidizer in place.

10. A patient interface system according to claim 9, wherein the retaining means are formed on or in the at least one strap.

11. A patient interface system according to claim 1, wherein the at least one rigidizer comprises two rigidizers, wherein the at least one strap comprises two pockets, each of the two pockets being configured enclose and abut the second free end of each of the two rigidizers to limit movement of the at least one strap relative to the two rigidizers at the second free end of each of the two rigidizers in use.

12. A patient interface system according to claim 1, wherein the at least one strap comprises a sleeve arranged to receive and hold the at least one rigidizer, and wherein the at least one strap is configured to move substantially axially relative to the at least one rigidizer.

13. A patient interface system according to claim 1, wherein the at least one strap is configured to take the shape of the at least one rigidizer in use, and wherein the at least one rigidizer is configured to impart the shape of the at least one rigidizer to the at least one strap to direct pressure from the headgear to portions of a wearers' face in use.

14. A patient interface system according to claim 1, wherein the at least one rigidizer and the strap are affixed in a limited area that is adjacent to a pocket or a sleeve opening of the strap.

15. A patient interface system according to claim 1, wherein the at least one strap comprises a sleeve arranged to receive and hold the at least one rigidizer.

16. A patient interface system according to claim 15, wherein the at least one strap is configured to receive and hold the at least one rigidizer by sowing, welding, gluing, heat staking, clamping, buttoning, snapping a cover over the at least one rigidizer, and/or snapping on an external part.

17. A patient interface system according to claim 16, wherein snapping on an external part is achieved by aligning the at least one strap and the at least one rigidizer and pushing the at least one rigidizer inside the sleeve and fixing both the at least one strap and the at least one rigidizer to the external part.

18. A patient interface system according to claim 1, wherein a point at which the at least one rigidizer is fixed to the at least one strap is located at one end of the at least one rigidizer.

19. A patient interface system according to claim 1, wherein the at least one rigidizer is more rigid than the at least one strap.

20. A patient interface system according to claim 1, wherein the at least one strap is made of an elastomeric material, the elastomeric material comprising elastane, TPE, or silicone, or the at least one strap is made of a combination of any of elastane, TPE, or silicone with one another or with other materials.

21. A patient interface system according to claim 1, wherein the headgear further comprises elastic walls that are woven, knitted, braided, molded, and/or extruded.

22. A patient interface system according to claim 1, wherein the at least one rigidizer comprises two or more rigidizers, each arranged to be symmetrically disposed on a corresponding side of the patient's face.

23. A patient interface system according to claim 1, wherein the headgear, including the at least one strap, is made of stretchable textile.

24. A patient interface system according to claim 1, wherein the at least one strap is removable from the at least one rigidizer.

25. A patient interface system according to claim 1, wherein the at least one strap maintains its entire operational length and is able to freely stretch along the at least one rigidizer during use.

26. A patient interface system according to claim 1, wherein the at least one strap is in the form of a sleeve arranged to slip over the rigidizer such that the at least one strap maintains its stretchable length and is able to substantially freely stretch over the at least one rigidizer during use.

27. A patient interface system according to claim 1, wherein the at least one strap comprises more than two straps, a respective end of each strap being arranged for hinged connection to another strap and/or the mask frame.

28. A patient interface system according to claim 1, wherein the headgear is arranged to support the patient interface on the patient's face during use, said patient interface comprising one of a nasal cannula, nasal prongs, or a respiratory mask configured to cover the nose and/or the mouth of the patient in use.

29. A patient interface system according to claim 1, wherein the at least one strap is a hollow tube with at least one opening structured to receive the at least one rigidizer.

30. A patient interface system according to claim 1, wherein the at least one strap further comprises two side straps configured to extend from the mask frame along corresponding sides of a user's head in use and two back straps configured to extend along the back of the user's head in use, and
   wherein each of the two side straps and each of the two back straps are made of the elastic material.

31. A patient interface system according to claim 30, wherein each of the two side straps are wider than each of the two back straps and each of the two back straps are equal in length.

32. A patient interface system according to claim 31, wherein the two back straps are not adjustable except through stretching due to elasticity of the two back straps.

33. A patient interface system according to claim 30, wherein tension vectors of the two side straps are adjustable by moving the two back straps relative to one another at the back of the patient's head in use.

34. A patient interface system according to claim 30, wherein a distribution of the applied force of the two back straps is adjustable by moving the back straps relative to one another at the back of the patient's head in use.

35. A patient interface system according to claim 30, wherein a distribution of the applied force of the two back straps is adjustable by independently changing a position of each of the two back straps.

36. A patient interface system according to claim 30, wherein the at least one rigidizer further comprises two rigidizers, and
   wherein each of the two side straps includes an opening through which a corresponding one of the two rigidizers is able to be inserted or removed.

37. A patient interface system according to claim 36, wherein each opening is located on an outer surface of the respective side strap that faces away from the patient in use.

38. A patient interface system according to claim 36, wherein each opening has a slit shape.

39. A patient interface system according to claim 36, wherein each opening is shaped as an elongate extension.

40. A patient interface system according to claim 39, wherein each opening extends substantially coaxial to the longitudinal axis of the respective strap and the respective rigidizer.

41. A patient interface system according to claim 1, wherein the at least one strap comprises three or more separate straps connected by two or more joins.

42. A patient interface system according to claim 1, wherein the at least one rigidizer is connected to the mask frame.

43. A patient interface system according to claim 1, wherein the length of the at least one strap is adjustable to fit a range of head sizes by stretching the first portion of the at least one strap along a portion of the at least one rigidizer and past the first free end of the at least one rigidizer.

44. A patient interface system according to claim 1, wherein multiple points for attachment between the at least one strap and the at least one rigidizer may be provided such that one or more fixation locations may be chosen and varied to allow adjustment of an elastic length of the at least one strap.

* * * * *